United States Patent
Guétat et al.

(10) Patent No.: US 7,650,025 B2
(45) Date of Patent: Jan. 19, 2010

(54) SYSTEM AND METHOD FOR BODY EXTRACTION IN MEDICAL IMAGE VOLUMES

(75) Inventors: Grégoire Guétat, Talant (FR); Jonathan Stoeckel, RB Hierden (NL); Matthias Wolf, Coatesville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 715 days.

(21) Appl. No.: 11/493,308

(22) Filed: Jul. 26, 2006

(65) Prior Publication Data

US 2007/0036411 A1 Feb. 15, 2007

Related U.S. Application Data

(60) Provisional application No. 60/704,349, filed on Aug. 1, 2005.

(51) Int. Cl.
*G06K 9/00* (2006.01)
(52) U.S. Cl. .................. 382/128; 382/131; 382/132; 378/151
(58) Field of Classification Search .......... 382/128, 382/131, 132, 173, 181; 378/151
See application file for complete search history.

(56) References Cited

U.S. PATENT DOCUMENTS 5,825,910 A * 10/1998 Vafai .................. 382/132

6,055,295 A * 4/2000 Murthy et al. .......... 378/151

OTHER PUBLICATIONS

Guétat et al., "A Fast Algorithm for Body Extraction in CT Volumes", Proceedings of SPIE, Medical Imaging 2006: Image Processing (Online), vol. 6144, Mar. 15, 2006.
Park et al., "A non-self intersecting adaptive deformable surface for complex boundary extraction from volumetric images", Computers and Graphics, Pergamon Press Ltd, Oxford, GB, vol. 25, No. 3, Jun. 2001, pp. 421-440.
McInerney et al., "Topology Adaptive Deformable Surfaces for Medical Image Volume Segmentation", IEEE Transactions on Medical Imaging, IEEE Service Center, Piscataway, NJ, US, vol. 18, No. 10, Oct. 1999, pp. 840-850.
McInerney et al., "Deformable Models in Medical Analysis: A Survey", Medical image Analysis, Oxford University Press, Oxford, GB, vol. 1, No. 2, Jun. 1996, pp. 91-108.
Chuang et al., "Fast and accurate active contours for object boundary segmentation", Circuits and Systems, 2000, IEEE APCCAS 2000, The 2000 IEEE Asia-Pacific Conference on Dec. 4-6, 2000, Piscataway, NJ, USA, IEEE, Dec. 4, 2000, pp. 473-476.
Michael Kass, et al., "Snakes: Active Contour Models", *International Journal of Computer Vision*, 321-331 (1988).
Tim McInerney, et al., "Deformable Models in Medical Image Analysis a Survey," *Published in Medical Image Analysis*, 1(2); 91-108, 1996.

* cited by examiner

*Primary Examiner*—Tom Y Lu

(57) ABSTRACT

A method for identifying non-body structures in digitized medical images including the steps of providing a digitized image comprising a plurality of intensities corresponding to a domain of points on an N-dimensional grid, wherein said image includes a representation of a body and of non-body structures separate from said body, initializing a surface in said image on a side of said non-body structures opposite from said body, defining a plurality of forces acting on said surface, and displacing said surface through said non-body structures using said forces until said body is encountered.

28 Claims, 6 Drawing Sheets

| Number of slices | <300 | 300-400 | 400-550 | >550 | Any |
|---|---|---|---|---|---|
| Number of corresponding volumes | 39 | 32 | 27 | 17 | 115 |
| Average Time (s) | 3.73 | 5.16 | 6.94 | 9.22 | 5.70 |
| Standard Deviation (s) | 1.39 | 1.59 | 1.33 | 2.78 | 2.54 |
| Min (s) | 0.66 | 2.89 | 4.09 | 5.61 | 0.66 |
| Max (s) | 6.30 | 8.43 | 9.89 | 14.75 | 14.75 |

A

B

C

D

E

F

A1　　　　　　　　　　　　A2

B1　　　　　　　　　　　　B2

SYSTEM AND METHOD FOR BODY EXTRACTION IN MEDICAL IMAGE VOLUMES

CROSS REFERENCE TO RELATED UNITED STATES APPLICATIONS

This application claims priority from "System for the Removal of Non-Body Structures in CT Images", U.S. Provisional Application No. 60/704,349 of Guetat, et al., filed Aug. 1, 2005, the contents of which are incorporated herein by reference.

TECHNICAL FIELD

This invention is directed to processing and segmentation of digitized medical images.

DISCUSSION OF THE RELATED ART

The diagnostically superior information available from data acquired from current imaging systems enables the detection of potential problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital images are created from an array of numerical values representing a property (such as a grey scale value or magnetic field strength) associable with an anatomical location points referenced by a particular array location. The set of anatomical location points comprises the domain of the image. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels. Computer-aided diagnosis ("CAD") systems play a critical role in the analysis and visualization of digital imaging data.

The computed tomography (CT) imaging modality shows not only the body of the patient in the volumes it generates, but also his/her clothing, the cushion and the table. In 3D visualization, high density portions of the table often occlude some regions of interest such as the spine of the patient. Moreover, because the shape of the table and cushions may differ from one acquisition to another, or might be present in only one of them, this could present issues when registering volumes obtained at different time points for comparison, especially for two applications. The first is 3D visualization, where the table has high density parts that might hide regions of interest. The second is registration of acquisitions obtained at different time points; indeed, the table and cushions might be visible in one data set only, and their positions and shapes may vary, making the registration less accurate.

SUMMARY OF THE INVENTION

Exemplary embodiments of the invention as described herein generally include methods and systems for automatically extracting the body from CT images and remove all parts of no interest, meaning essentially the table together with the cushions. A multi-scale method based on deformable models moves a surface across an image that attaches to the boundaries of the body. One iteratively computes forces which take into account local information around the surface. These forces make the surface move through the table but ensure that it stops when coming close to the body. The model has elastic properties, that take into account the fact that some regions in the volume convey more information than others by giving them more weight. This is done by using normalized convolution when regularizing the surface. An algorithm according to an embodiment of the invention was tested on a database of over a hundred volumes of whole body, chest or lower abdomen, and has proven to be efficient, even for volumes with up to 900 slices, providing accurate results in an average time of 6 seconds. It is also robust against noise and variations of scale and shape of the table, reliable, and fast.

DETAILED DESCRIPTION OF THE PREFERRED EMBODIMENTS

Figures 1, 4:
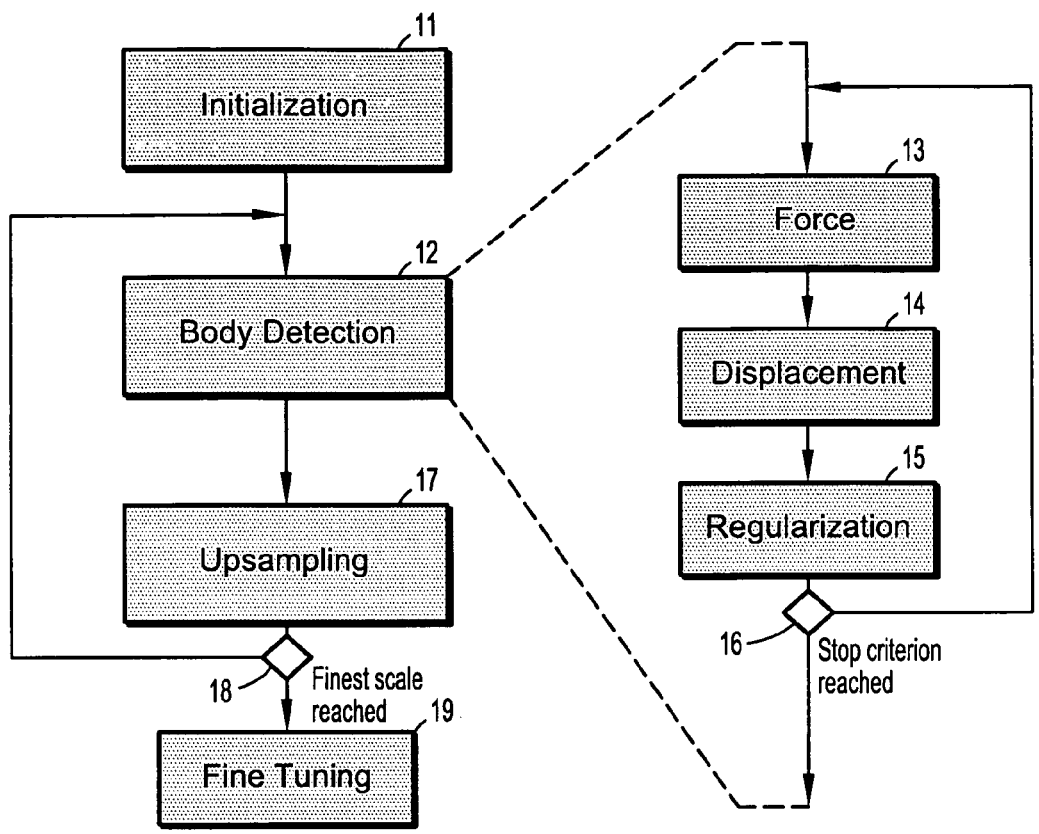
FIG. 1 depicts a flow chart of a body extraction method according to an embodiment of the invention.
FIG. 4 depicts a table results on the whole database according to an embodiment of the invention.

Exemplary embodiments of the invention as described herein generally include systems and methods for automatically extracting the body from medical images. An exemplary medical imaging modality is that of computed topography (CT), however, embodiments of the invention are applicable to any 3-dimensional imaging modality. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A method for removing non-body structures from a medical image according to an embodiment of the invention faces several challenges. In some cases, the table might not be present in the image, in which case the method should not remove any structure from the image. Sometimes a table includes a cushion or head-rest, however, because of their deformability, no a priori information about their shape can be assumed. At the contact point between the patient and the table, a method should be able to distinguish the table form the patient. Images are frequently noisy, blurring object boundaries. In addition, occlusions may be present, in which case a method should only remove what is necessary. The objects-of-interest in the images, such as intestines, lungs, heart, skeleton, etc. come in a variety of shapes and scales. Sometimes, structural elements in the table can resemble anatomical structures, such as high intensity structural blocks, which have an image intensity range similar to that of bone structures.

A method according to an embodiment of the invention uses an original adaptation of the deformable model which does not require any user interaction and works within a very short amount of time, making it useable in existing medical 3D visualization workstations. It needs only to compute image features locally, contrary to other methods which need to compute the features globally prior to the iterative process. The use of deformable elastic models in medical imaging was introduced by Terzopoulos in 1988. Deformable models can simulate the behavior of non-rigid physical objects having elastic properties, and are evolved to find the state of minimum energy. These models typically incorporate two types of forces: (1) internal forces, which characterize the deformation of a stretchable flexible contour; and (2) external forces, which characterize the image volume, where extrema coincide with edges, intensity extrema, etc.

The best known deformable models are referred to as snakes. Snakes are planar deformable contours that are useful in several image analysis tasks. They are often used to approximate the locations and shapes of object boundaries in images based on the reasonable assumption that boundaries are piecewise continuous or smooth. In its basic form, the mathematical formulation of snakes draws from the theory of optimal approximation involving functionals.

Geometrically, a snake is a parametric contour embedded in the image plane (x, y)∈R. The contour is represented as $v(s)=(x(s), y(s))^T$, where x and y are the coordinate functions and s∈[0,1] is the parametric domain. The shape of the contour subject to an image I(x; y) is dictated by the functional $$E(v)=S(v)+P(v).$$

This functional can be viewed as a representation of the energy of the contour and the final shape of the contour corresponds to the minimum of this energy. The first term of the functional, $$S(v) = \int_0^1 \left( w_1(s) \left| \frac{\partial v}{\partial s} \right|^2 + w_2(s) \left| \frac{\partial^2 v}{\partial^2 s} \right|^2 \right) ds,$$

is the internal deformation energy. It characterizes the deformation of a stretchy, flexible contour. Two physical parameter functions dictate the simulated physical characteristics of the contour: $w_1(s)$ controls the "tension" of the contour while $w_2(s)$ controls its "rigidity". The values of the non-negative functions $w_1(s)$ and $w_2(s)$ determine the extent to which the snake can stretch or bend at any point s on the snake. For example, increasing the magnitude of $w_1(s)$ increases the "tension" and tends to eliminate extraneous loops and ripples by reducing the length of the snake. Increasing $w_2(s)$ increases the bending "rigidity" of the snake and tends to make the snake smoother and less flexible. Setting the value of one or both of these functions to zero at a point s permits discontinuities in the contour at S. The second term in (1) couples the snake to the image. The second term typically takes the form $$P(v) = \int_0^1 P(v(s))ds,$$

where P(x,y) denotes a scalar potential function defined on the image plane. To apply snakes to images, external potentials are designed whose local minima coincide with intensity extrema, edges, and other image features of interest. For example, the contour will be attracted to intensity edges in an image I(x,y) by choosing a potential $$P(x, y)=-c|\nabla[G_\sigma * I(x, y)]|,$$

where c controls the magnitude of the potential, $\nabla$ is the gradient operator, and $G_\sigma * I$ denotes the image convolved with a (Gaussian) smoothing filter whose characteristic width $\sigma$ controls the spatial extent of the local minima of P.

According to the calculus of variations, the contour v(s) which minimizes the energy E(v) satisfies the Euler-Lagrange equation $$-\frac{\partial}{\partial s}\left(w_1 \frac{\partial v}{\partial s}\right) + \frac{\partial^2}{\partial s^2}\left(w_2 \frac{\partial^2 v}{\partial s^2}\right) + \nabla P(v(s, t)) = 0.$$

This vector-valued partial differential equation expresses the balance of internal and external forces when the contour rests at equilibrium. The first two terms represent the internal stretching and bending forces, respectively, while the third term represents the external forces that couple the snake to the image data. The usual approach to solving this equation is through the application of numerical algorithms.

While it is natural to view energy minimization as a static problem, a potent approach to computing the local minima of a functional is to construct a dynamical system that is governed by the functional and allow the system to evolve to equilibrium. The system may be constructed by applying the principles of Lagrangian mechanics. This leads to dynamic deformable models that unify the description of shape and motion, making it possible to quantify not just static shape, but also shape evolution through time. Dynamic models are valuable for medical image analysis, since most anatomical structures are deformable and continually undergo non-rigid motion in vivo. Moreover, dynamic models exhibit intuitively meaningful physical behaviors, making their evolution amenable to interactive guidance from a user.

A simple example is a dynamic snake which can be represented by introducing a time-varying contour v(s,t)=(x(s,t),y $(s,t))^T$ with a mass density $\mu(s)$ and a damping density $\gamma(s)$. The Lagrange equations of motion for a snake with the internal energy and external energy given above is $$\mu \frac{\partial^2 v}{\partial t^2} + \gamma \frac{\partial v}{\partial t} - \frac{\partial}{\partial s}\left(w_1 \frac{\partial v}{\partial s}\right) + \frac{\partial^2}{\partial s^2}\left(w_2 \frac{\partial^2 v}{\partial s^2}\right) = -\nabla P(v(s,t)).$$

The first two terms on the left hand side of this partial differential equation represent inertial and damping forces, while the remaining terms represent the internal stretching and bending forces, while the right hand side represents the external forces. Equilibrium is achieved when the internal and external forces balance and the contour comes to rest (i.e., $\partial v/\partial t = \partial^2 v/\partial t^2 = 0$), which yields the equilibrium condition.

According to an embodiment of the invention, a deformable elastic model involves a surface moving through the image. The surface crosses the table, but is stopped by the body's boundaries. The table is located below the patient, and the orientation of the table in the image is given by the DICOM header included with the image. The surface is initialized to be at the bottom of the image, and is represented by a matrix that contains the vertical coordinates of each pixel in the surface. The surface is moved upward to detect the body and deformed in the process, in directions determined by vectors normal to the surface. A vector normal to the surface at a point can be determined from the gradient of the average image intensity in the neighborhood of the surface point. This can be obtained by convolving the image with a Gaussian kernel of the form $$-\frac{x}{\sigma^3 \sqrt{2\pi}} \exp\left(-\frac{x^2}{2\sigma^2}\right)$$

and then extracting partial derivatives.

Figure 2:
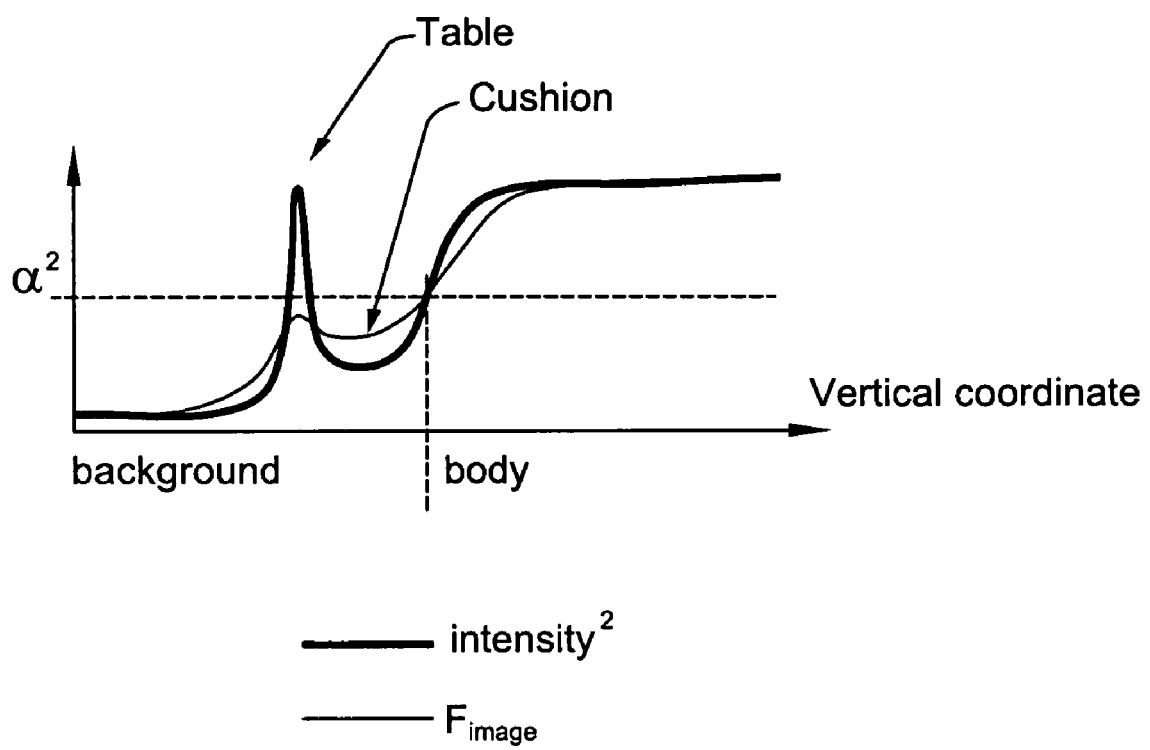
FIG. 2 is a graph illustrating the balance between the gravity-like force and the image force, according to an embodiment of the invention.

In order to control the motion of the surface through the image, a plurality of forces can be defined that act on the surface. An exemplary, non-limiting force includes three components. A first force is a gravity-like force that causes the surface go up to the body. The gravity-like force, defined as $F_{gravity} = \alpha^2$, where $\alpha$ is a value corresponding to the intensity value at the border of the body, causes the surface to move up toward the patient's body. A second force takes into account the average intensity in the neighborhood of the surface, so as to compensate for the gravity when the surface comes close to the body. The image force, defined as $F_{image}(x) = \text{average}(I(x))^2$ for all points in a neighborhood of x, takes into account the image features, and balances $F_{gravity}$ when the surface is close to the body. Both $F_{gravity}$ and $F_{image}$ are external forces. FIG. 2 is a graph illustrating the balance between the gravity-like force and the image force, according to an embodiment of the invention. The total external force is $F_{ext} = F_{image} + F_{gravity}$, with the force vectors pointing in opposite directions. The horizontal dotted line in the figure indicates $\alpha^2$, the magnitude of the gravity-like force, while the gray curve indicates the magnitude of $F_{image}$. The magnitude of the intensity is indicated by the black curve. Note that the curves intersect the $\alpha^2$ line by the vertical dotted line, which indicates where the body begins in the intensity. As can be seen, the force $F_{ext} = 0$ at the border of the body, where the average intensity=$\alpha$. $F_{ext} > 0$ if the surface penetrates the body, and $F_{ext} < 0$ outside the body.

In addition, there is a third force, and elastic force that models the elastic properties of the surface, and is calculated implicitly in a regularization step. As some regions of the volume convey more information than others, they are allotted more weight in the computation of this internal force. In particular, the parts of the surface located in a region with high gradient intensity are allocated more weight than parts located in uniform intensity areas. An issue that arises in the motion of the surface is that the surface might not stop at the border of the body, and might remove parts of the body from the image. To prevent this, a regularization step is used, in which the elasticity of the surface is introduced as an additional internal force. This force is calculated using a Gaussian kernel and controls the stiffness of the surface. This issue is dealt with by allocating more weight to points of the surface located in regions of interest in the image. These weights are used in the computation of the elasticity of the model to take into account the fact that some regions in the volume convey most of the information. According to an embodiment of the invention, a region of interest is a region with a high gradient magnitude. The additional weight makes the surface more rigid when it is close to the body, as recognized by high gradients. In other words, the weights are used to change the elasticity of the surface for pixels with a high gradient. The surface can then be regularized with a normalized convolution to take into account these weights:

$$\text{regularized surface} = \frac{\text{surface} \otimes \text{kernel}}{\text{weight} \otimes \text{kernel}}.$$

Figure 3:
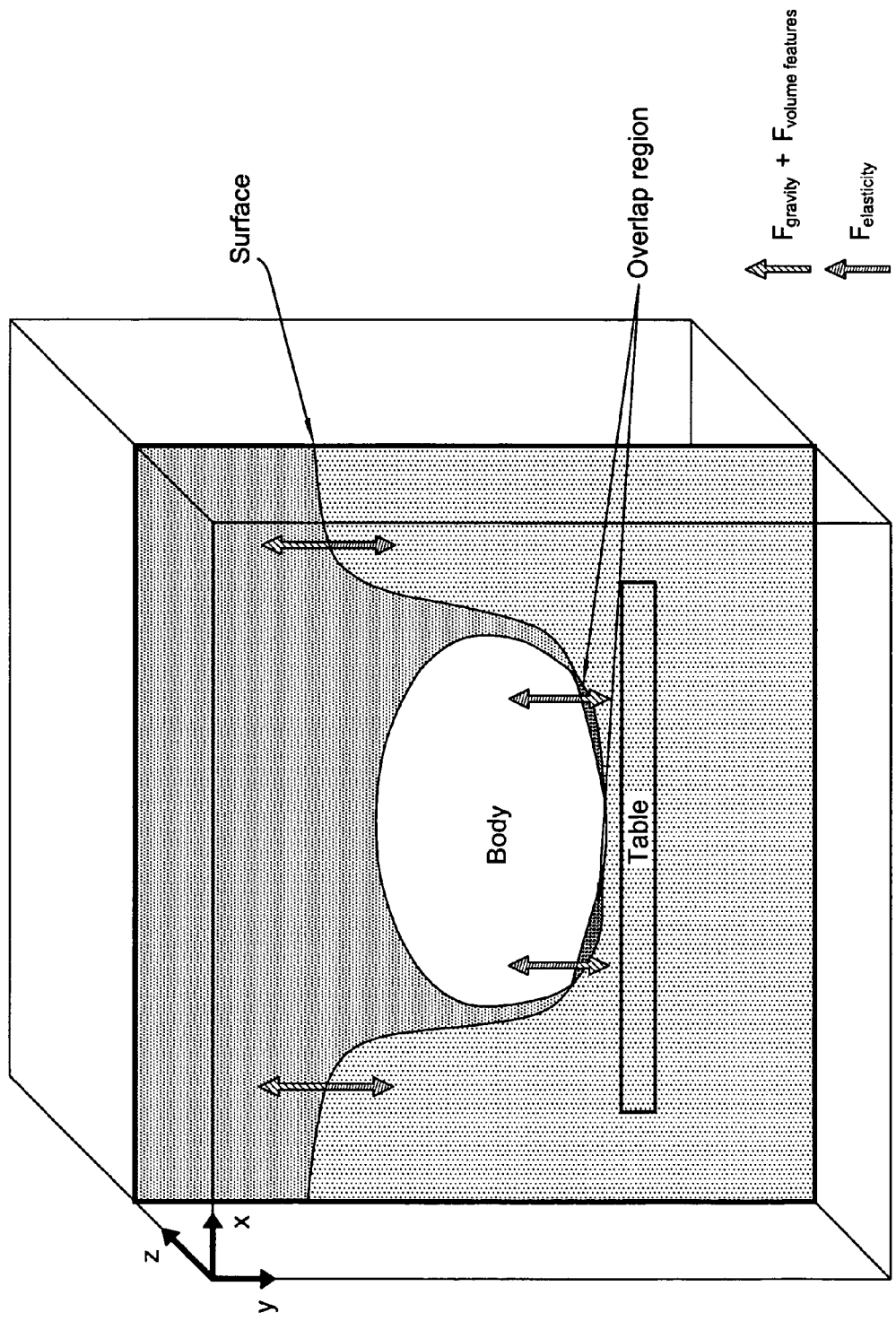
FIG. 3 illustrates the balance of forces on a body, according to an embodiment of the invention.

FIG. 3 illustrates the balance of forces on a body, according to an embodiment of the invention. Referring to the figure, the surface is indicated by the interface of the gray and black regions, and the body is the white region. The elastic forces are indicated by the black arrows, while the external forces that advance the surface are indicated by the gray arrows. The region where the surface overlaps the body is indicated by arrows, where the gray surface overlaps the white body.

In addition, to ensure that the surface does not penetrate the patient's body at all, a method according to an embodiment of the invention includes a fine tuning step. Fine tuning assumes that the surface has crossed the table and s is already close to the body. For all points on the surface, high intensity points are points in the patient's body, and low intensity points are in the background. The fine tuning can ensure that regions of interest are not removed from the final image, and allows the surface to be moved closer to the body. According to an embodiment of the invention, an adjustment is performed wherein all points in high intensity regions are moved down to low intensity regions. The steps of adjustment and regularization are performed for a fixed number of iterations and the step of fine tuning is performed after the last iteration has finished.

According to an embodiment of the invention, a multi-scale framework is introduced that enables a reduction of the computational load necessary to obtain local information around the surface, as well as to adapt the weights of the several parameters to the features of interest at the current resolution. Downsampling is performed in a multi-scale framework to improve time efficiency. Downsampling is accomplished by reducing the size of the image volume. For example, for downsampling by one level, one would use only every 2nd column, every 2nd row, and every 2nd slice of the image volume. For a 2-level downsampling, one would use only every 4th column, row, and slice. For a 3-level downsampling, it would be every 8th column, row, and slice and so forth. Essentially, an n-level downsampling uses every $2^n$th column, row, and slice.

According to an embodiment of the invention, a 3-level downsampling is used initially to make the surface move upwards faster. Once the contour of the body has been reached, a process according to an embodiment of the invention switches to a volume with a higher resolution, by incorporating some of the data previously not used. This technique is referred to as upsampling. The coordinates of the surface are transformed to the new coordinate system and the movement of the surface is continued at a higher resolution. This whole concept of starting at a lower resolution and increasing the resolution based on the intermediate results is also called multi-scale approach. The effect is that the surface moves much faster while away from the body and slows down when it approaches the body. Upsampling is continued until a finest scale of resolution is reached. The finest scale is the original resolution where all pixels are used. Theoretically this could also be any other level and can be defined based on the application.

A flow chart of a body extraction method according to an embodiment of the invention is shown in FIG. 1. A method according to an embodiment of the invention is based on the physical model of elastic deformable models, implemented in a multi-scale framework. Referring to the flow chart, a surface is initialized at step 11 at the bottom of the image, below the patient and the table, and the external forces are defined that will move the surface iteratively through the table but stop at the surface of the body. The 3-level downsampling of the image volume is performed, and the forces are initialized on this downsampled volume. At step 12, the surface is moved upward until the body is detected. This step includes steps 13 to 16. At step 13, the external forces acting on the surface are calculated, and the surface is displaced accordingly at step 14. The displaced surface is regularized at step 15. Step 16 loops back to repeat steps 13, 14, and 15 until the surface has approached and is close to the body. The stop criterion at step 16 is satisfied when the number of modified surface pixels in the last iteration is below a predetermined threshold. At step 17, an upsampling is performed, and step 18 loops steps 12 to 17 until the upsampling reaches the finest resolution scale permitted by the image or the application. Then, at step 19, fine tuning, is performed. Finally, those parts of the image traversed by the surface are removed from the image or otherwise processed to reduce their visibility in the image.

Results

A method according to an embodiment of the invention has been tested without any human interaction on a database of 115 CT volumes coming from several hospitals. In this database, volumes are found from several parts of the body: full body, chest or lower abdomen. The size of the volumes ranges from 512×512×53 voxels to 512×512×883, with an average resolution of 0.83×0.83×1.77 millimeters per voxel.

In this dataset, the table and cushions are not always present (being outside of the reconstruction area), or only partially, some volumes are very noisy, the table has in some cases a solid dense inner structure element with high density, and some patients have parts of their body in direct contact with the high-density part of the table.

Figure 5:
FIGS. 5(A)-(F) depict a superposition of the original image and of the mask generated by the algorithm according to an embodiment of the invention.
Figure 5:
Figure 5:
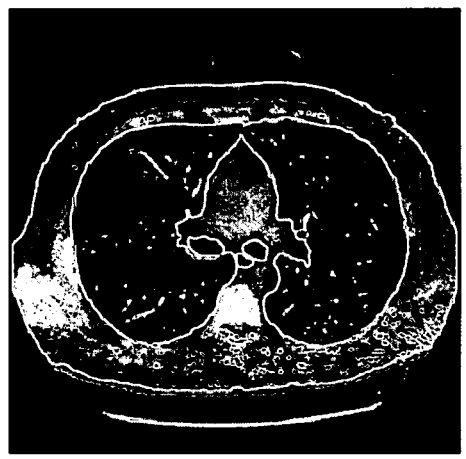
Figure 5:
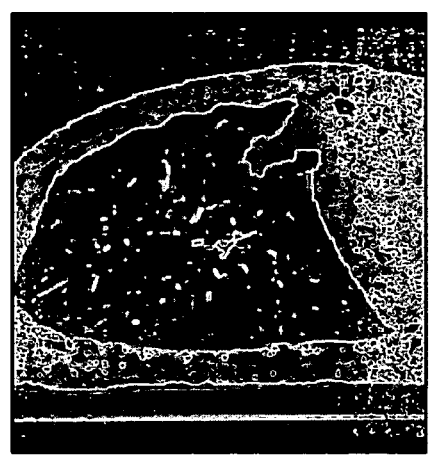
Figure 5:
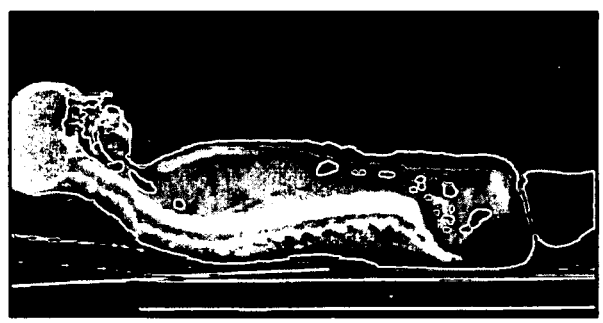
Figure 5:
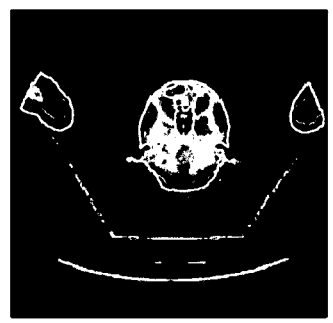

FIG. 4 is a table of results of an algorithm on the whole database, on a system using Intel® Xeon™ processor running at 3.06 GHz. The columns of the table are arranged by the number of slices. The table of FIG. 4 shows the number of corresponding volumes, average, standard deviation, minimum and maximum time necessary to run the algorithm for the volumes in the database. To validate the accuracy of an algorithm according to an embodiment of the invention, a visual inspection has been made for all volumes, both slice by slice and using a 3D renderer. In no case have any body parts been removed, while the table has always been completely removed. Additional results are shown in FIGS. 5 and 6.

FIGS. 5(A)-(F) depict the superposition of the original image and of the mask generated by the algorithm according to an embodiment of the invention. FIG. 5(A) shows an axial view of a patient with zoom of the region between the arm and the body of the patient. FIG. 5(B) shows a coronal view of a patient, specifically an example where the algorithm starts both from the top and the bottom of the patient. FIGS. 5(C)-(D) depict coronal and axial views of a patient. Note that the segmentation has been successful despite the noise in the image. FIGS. 5(E)-(F) depict coronal and axial views of a patient. Here, the head support has been removed but details of the body such as the ears are retained.

Figure 6:
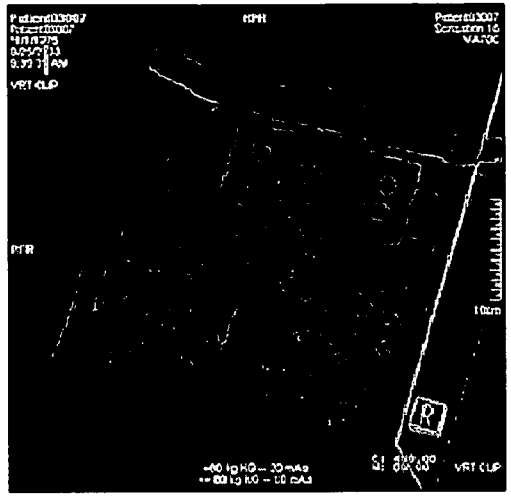
FIGS. 6(A1)-(B2) depicts comparisons of images obtained from a 3D visualization application according to an embodiment of the invention.
Figure 6:
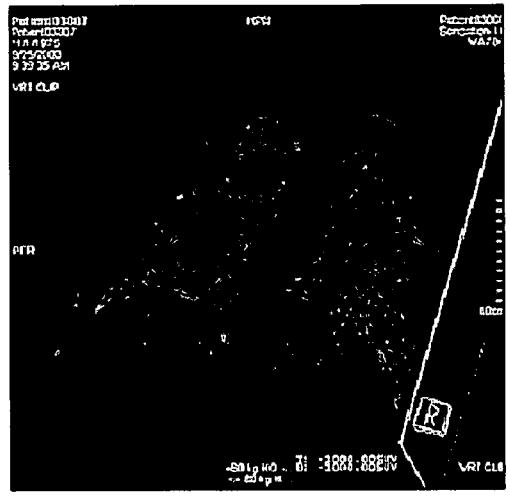
Figure 6:
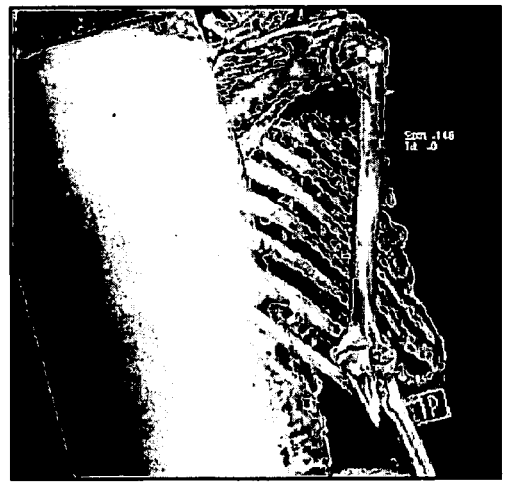
Figure 6:
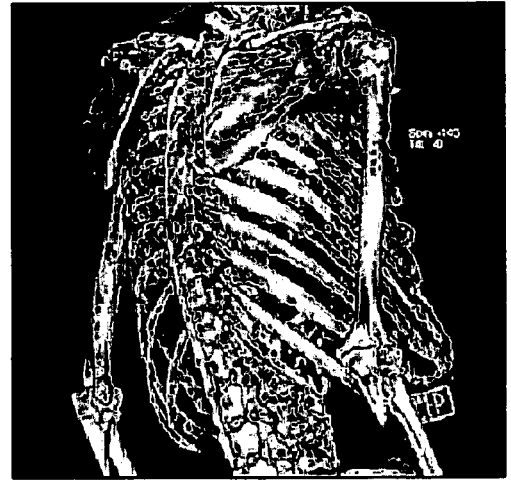

FIGS. 6(A1)-(B2) depict comparisons of images obtained from a 3D visualization application, using pre-established presets, according to an embodiment of the invention. FIG. 6(A1) depicts a view of the lungs (preset "Lungs") in an original image. FIG. 6(A2) shows the corresponding view after applying a body extracting method according to an embodiment of the invention. FIG. 6(B1) illustrates a view of the spine (preset "Spine Shaded") in an original image. FIG. 6(B2) illustrates the corresponding view after applying a body extracting method according to an embodiment of the invention.

In particular, FIG. 5(B) shows that an algorithm according to an embodiment of the invention might also be useful to remove medical equipment on top of the patient. According to an embodiment of the invention, the surface was initialized at the top of the image and it was moved downwards until it attached to the body. A method according to an embodiment of the invention to automatically extract the patient's body from CT volumes provides very good results while being fast and using little memory. The use of deformable elastic surfaces appears to be an efficient way of segmenting large regular structures in 3D volumes.

System Implementation

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 7:
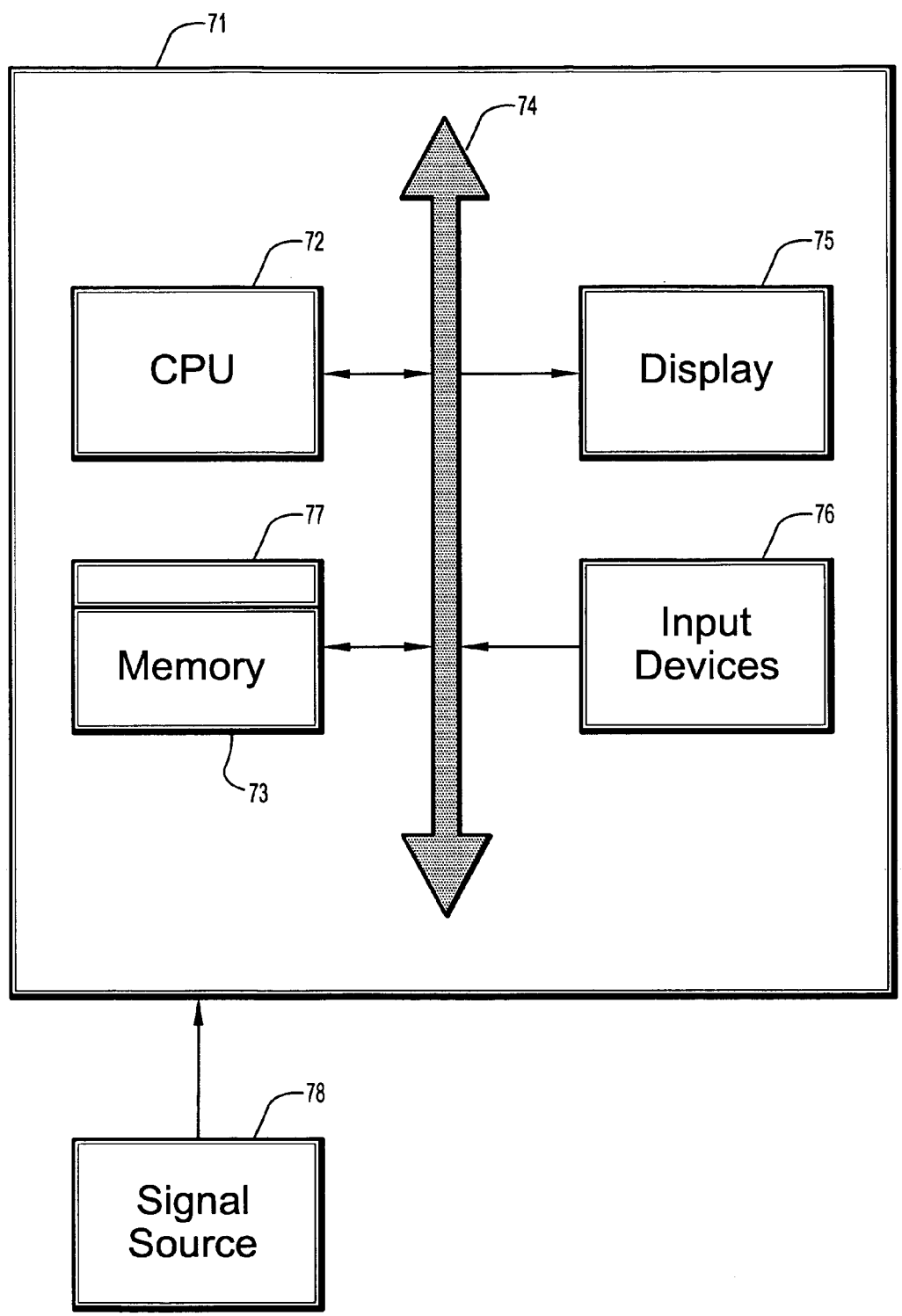
FIG. 7 is a block diagram of an exemplary computer system for implementing a body extraction method according to an embodiment of the invention.

FIG. 7 is a block diagram of an exemplary computer system for implementing a body extraction method according to an embodiment of the invention. Referring now to FIG. 7, a computer system 71 for implementing an embodiment of the present invention can comprise, inter alia, a central processing unit (CPU) 72, a memory 73 and an input/output (I/O) interface 74. The computer system 71 is generally coupled through the I/O interface 74 to a display 75 and various input devices 76 such as a mouse and a keyboard. The support circuits can include circuits such as cache, power supplies, clock circuits, and a communication bus. The memory 73 can include random access memory (RAM), read only memory (ROM), disk drive, tape drive, etc., or a combinations thereof. The present invention can be implemented as a routine 77 that is stored in memory 73 and executed by the CPU 72 to process the signal from the signal source 78. As such, the computer system 71 is a general purpose computer system that becomes a specific purpose computer system when executing the routine 77 of the present invention.

The computer system 71 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of identifying non-body structures in digitized medical images comprising the steps of:
    providing a digitized image comprising a plurality of intensities corresponding to a domain of points on an N-dimensional grid, wherein said image includes a representation of a body and of non-body structures separate from said body;
    initializing a surface in said image on a side of said non-body structures opposite from said body;
    defining a plurality of forces acting on said surface; and
    displacing said surface through said non-body structures using said forces until said body is encountered.

2. The method of claim 1, further comprising removing those structures traversed by said surface from said image.

3. The method of claim 1, wherein said plurality of forces includes a first, external, force to move said surface toward said body, wherein said first force has a constant magnitude based on the image intensity value at the border of said body.

4. The method of claim 3, wherein said plurality of forces includes a second, external, force that acts opposite to first force, wherein the magnitude of said second force at a point on the surface is proportional to the square of the average image intensity in the neighborhood of said surface point.

5. The method of claim 4, wherein said plurality of forces includes a third, internal, force, wherein the magnitude of said third force at a point on the surface is proportional to the magnitude of the gradient of an average image intensity in the neighborhood of said point.

6. The method of claim 3, wherein a vector sum of said first and second forces is zero at the border of said body.

7. The method of claim 1, wherein said plurality of forces are defined wherein said surface does not penetrate said body.

8. The method of claim 1, wherein a direction of surface propagation at a point on said surface is determined by a gradient of an average image intensity in the neighborhood of said surface point.

9. The method of claim 8, wherein said average image intensity is obtained by convolving said image with a Gaussian kernel in said neighborhood.

10. The method of claim 1, further comprising regularizing said surface after a displacement, wherein said regularized surface is a ratio of a convolution of said displaced surface with a Gaussian kernel and a convolution of a weighting functions with said Gaussian kernel, wherein said weighting function at a point is proportional to a magnitude of a gradient of an average image intensity in the neighborhood of said point.

11. The method of claim 1, further comprising downsampling said image when said surface is initialized.

12. The method of claim 11, further comprising upsampling said image as said surface approaches said body, and recalculating said surface in said upsampled image.

13. The method of claim 1, further comprising fine-tuning said surface when said surface makes contact with said body, wherein fine-tuning comprises moving points in high intensity regions to low intensity regions.

14. A method of identifying non-body structures in digitized medical images comprising the steps of:
    providing a digitized image comprising a plurality of intensities corresponding to a domain of points on an N-dimensional grid, wherein said image includes a representation of a body and of non-body parts separate from said body; and
    displacing said surface through said non-body structures using a plurality of forces acting on said surface until said body is encountered, wherein said plurality of forces includes a first external force to move said surface toward said body, wherein said first force has a constant magnitude based on the image intensity value at the border of said body, and a second, external, force that acts opposite to first force, wherein the magnitude of said second force at a point on the surface is proportional to the square of the average image intensity in the neighborhood of said surface point.

15. The method of claim 14, further comprising initializing said surface in said image on a side of said non-body structures opposite from said body.

16. A program storage device readable by a computer, tangibly embodying a program of instructions executable by the computer to perform the method steps for identifying non-body structures in digitized medical images; said method comprising the steps of:
    providing a digitized image comprising a plurality of intensities corresponding to a domain of points on an N-dimensional grid, wherein said image includes a representation of a body and of non-body structures separate from said body;
    initializing a surface in said image on a side of said non-body structures opposite from said body;
    defining a plurality of forces acting on said surface; and
    displacing said surface through said non-body structures using said forces until said body is encountered.

17. The computer readable program storage device of claim 16, the method further comprising removing those structures traversed by said surface from said image.

18. The computer readable program storage device of claim 16, wherein said plurality of forces includes a first, external, force to move said surface toward said body, wherein said first force has a constant magnitude based on the image intensity value at the border of said body.

19. The computer readable program storage device of claim 18, wherein said plurality of forces includes a second, external, force that acts opposite to first force, wherein the magnitude of said second force at a point on the surface is proportional to the square of the average image intensity in the neighborhood of said surface point.

20. The computer readable program storage device of claim 19, wherein said plurality of forces includes a third, internal, force, wherein the magnitude of said third force at a point on the surface is proportional to the magnitude of the gradient of an average image intensity in the neighborhood of said point.

21. The computer readable program storage device of claim 18, wherein a vector sum of said first and second forces is zero at the border of said body.

22. The computer readable program storage device of claim 16, wherein said plurality of forces are defined wherein said surface does not penetrate said body.

23. The computer readable program storage device of claim 16, wherein a direction of surface propagation at a point on said surface is determined by a gradient of an average image intensity in the neighborhood of said surface point.

24. The computer readable program storage device of claim 23, wherein said average image intensity is obtained by convolving said image with a Gaussian kernel in said neighborhood.

25. The computer readable program storage device of claim 16, the method further comprising regularizing said surface after a displacement, wherein said regularized surface is a ratio of a convolution of said displaced surface with a Gaussian kernel and a convolution of a weighting functions with said Gaussian kernel, wherein said weighting function at a point is proportional to a magnitude of a gradient of an average image intensity in the neighborhood of said point.

26. The computer readable program storage device of claim 16, the method further comprising downsampling said image when said surface is initialized.

27. The computer readable program storage device of claim 26, the method further comprising upsampling said image as said surface approaches said body, and recalculating said surface in said upsampled image.

28. The computer readable program storage device of claim 16, the method further comprising fine-tuning said surface when said surface makes contact with said body, wherein fine-tuning comprises moving points in high intensity regions to low intensity regions.

* * * * *